United States Patent
Bombardelli et al.

(10) Patent No.: US 6,475,536 B2
(45) Date of Patent: *Nov. 5, 2002

(54) PHARMACEUTICAL AND COSMETIC FORMULATIONS WITH ANTIMICROBIAL ACTIVITY

(75) Inventors: Ezio Bombardelli, Milan (IT); Paolo Morazzoni, Milan (IT); Aldo Cristoni, Milan (IT); Roberto Seghizzi, Milan (IT)

(73) Assignee: Indena S.p.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/884,939

(22) Filed: Jun. 21, 2001

(65) Prior Publication Data

US 2001/0046525 A1 Nov. 29, 2001

Related U.S. Application Data

(63) Continuation of application No. 09/301,687, filed on Apr. 29, 1999, now Pat. No. 6,267,996, and a continuation-in-part of application No. 09/254,040, filed as application No. PCT/EP97/05529 on Oct. 8, 1997, now abandoned, said application No. 09/301,687, is a continuation-in-part of application No. 09/254,038, filed as application No. PCT/EP97/05510 on Oct. 7, 1997, now abandoned.

(30) Foreign Application Priority Data

Oct. 17, 1996 (IT) .......................... MI96A2149
Oct. 17, 1996 (IT) .......................... MI96A2148

(51) Int. Cl.⁷ .................... A61K 35/78; A01N 65/00
(52) U.S. Cl. .................. 424/773; 424/725; 424/774; 424/775; 424/778
(58) Field of Search ....................... 424/725, 773, 424/774, 775, 778

(56) References Cited

U.S. PATENT DOCUMENTS

| | | | |
|---|---|---|---|
| 4,886,667 A | 12/1989 | Kitagaki et al. | 424/195 |
| 5,104,655 A | 4/1992 | Bombardelli et al. | 424/195 |
| 5,118,671 A | 6/1992 | Bombardelli et al. | 514/26 |
| 5,147,859 A | 9/1992 | Bombardelli et al. | 514/26 |
| 5,166,139 A | 11/1992 | Bombardelli et al. | 514/26 |

FOREIGN PATENT DOCUMENTS

| | | |
|---|---|---|
| EP | 0 283 713 | 9/1988 |
| EP | 0 304 603 | 3/1989 |
| EP | 0 464 297 A1 | 1/1992 |
| GB | 2 184 353 A | 3/1987 |
| GB | 2 274 058 | 7/1994 |
| IN | 139 868 A | 8/1976 |
| JP | 63-267714 | 11/1988 |
| JP | 8-12565 | 1/1996 |

OTHER PUBLICATIONS

Patent Abstract of Japan, vol. 096, No. 005, May 31, 1996 & JP 08 012565 A (Shiseido Co. Ltd.), Jan. 16, 1996.
Patent Abstract of Japan, vol. 013, No. 079 (C–571), Feb. 22, 1989 & JP 63 267714 A (Sato Seiyaku KK), Nov. 4, 1988.

Primary Examiner—Herbert J. Lilling
(74) Attorney, Agent, or Firm—Pennie & Edmonds LLP

(57) ABSTRACT

The present invention relates to novel antiacne compositions containing extract of Krameria, or a pure compound from the extract, at least one of ximeninic acid or lauric acid, and an anti-inflammatory saponin extracted from *Olax dissitiflora, Aesculus hippocastanum, Centella asiatica, Terminalia sericea, Glycyrrhiza glabra,* or mixtures thereof.

18 Claims, No Drawings

PHARMACEUTICAL AND COSMETIC FORMULATIONS WITH ANTIMICROBIAL ACTIVITY

CROSS-REFERENCE TO RELATED APPLICATIONS

This application is a continuation of U.S. application Ser. No. 09/301,687 filed on Apr. 29, 1999, now U.S. Pat. No. 6,267,996, which is a continuation-in-part of U.S. application Ser. No. 09/254,038, filed on Feb. 26, 1999, now abandoned, which is a U.S. National Phase entry of PCT EP 97/05510, filed on Oct. 7, 1997 and U.S. application Ser. No. 09/254,040, filed on Feb. 26, 1999, now abandoned, which is a U.S. National Phase entry of PCT EP 97/05529, filed on Oct. 8, 1997, the disclosures of which are hereby incorporated herein by express reference thereto.

BACKGROUND OF THE INVENTION

The present invention is directed to novel pharmaceutical and cosmetic formulations which exhibit antimicrobial activity including hydrophilic or pure extracts of Krameria and lipophilic extract of Mesua ferrea in a sufficient amount to exhibit antimicrobial activity.

Extracts of the roots, bark, and leaves of different species of Krameria are enriched in neolignanes which have antimicrobial activity against gram negative, gram positive bacteria, fungi, and anaerobic strains. (Martindale, The Extrapharmacopeia, 28th Ed. 1982; Cannizaro, Boll. Soc. Ital. Biol. Sperim. 1, 22, 1964; V. Hoppe, Drogenkunde Bdl Walter De Gruyter Ed., 1975; and British Patent 2,184,353 A). A preferred species of Krameria is *Krameria triandra*, and a particularly active neolignane is Eupomatenoid. The extracts are obtained by extraction with chlorinated solvents, aliphatic ethers and ketones, as well as aliphatic and aromatic esters.

The extracts of Krameria's roots, bark, and leaves are naturally hydrophilic due to the phenol character of their active components. Nevertheless, the extraction can be carried out with protic solvents. Pure Eupomatenoid 6 and 2-(2,4-dihydroxyphenyl)-5-propenylbenzofuran can be recovered from these extracts using chromatographic techniques on silica gel, as reported in EP 0 464 297 B 1.

Flowers, and particularly the buds, of *Mesua ferrea*, yield a lipophilic extract containing substituted coumarins and xanthones. These extracts are particularly active on gram negative, gram positive, and anaerobic bacterial strains, with an activity comparable to that of the extract prepared from *Krameria triandra*. The extraction can be carried out with aprotic solvents such as hexane, methylene chloride. However, for better results, the extraction process can be carried out with carbon dioxide in hyper-critic conditions. For example, the extraction of vegetable material is conducted under pressures ranging from 110 to 260 bar, mainly at 200 bar and at temperatures ranging from 35° C. to 65° C., preferably at 45° C.

Despite improvements in the extraction process of Krameria, the use of the extract or compounds within the extract with medications is still mostly undeveloped. Shortcomings include the absence of medications which use Krameria extracts in combination with other medications and a clear understanding of the effect of extract of Krameria upon other compounds. The present invention is directed to overcoming these shortcomings by providing cosmetic and pharmaceutical formulations including extract of Krameria and extract of *Mesua ferrea* and demonstrating their superior antimicrobial activity as compared to conventionally prepared compounds, i.e. compounds lacking extract of Krameria and extract of *Mesua ferrea*.

SUMMARY OF THE INVENTION

The present invention is directed to an antimicrobial or preservative formulation including an extract of Krameria in combination with an extract of *Mesua ferrea*. The extracts are present in a combined amount sufficient to inhibit microbial growth, including weight ratios of between about 10:1 to about 1:10, preferably between about 2:3 to about 3:2, and more preferably about 1:1. The Krameria extract is present in an amount of between about 0.01 percent to about 1 percent by weight, and is an extract of Krameria sp., extract of *Krameria triandra*, a neolignane, a pure compound of the extract, or a mixture thereof. The neolignane may be Eupomatenoid 6, 2-(2,4-dihydroxyphenyl)-5-propenylbenzofuran, or a mixture thereof. The *Mesua ferrea* extract is present in an amount of between about 0.1 percent to about 0.5 percent by weight.

The formulation may also comprise at least one ximeninic acid, in a amount of between about 0.1 percent to about 0.5 percent by weight; lauric acid, in an amount of between about 0.1 percent to about 0.4 percent by weight; and an anti-inflammatory saponin, in an amount between about 0.1 percent to about 1 percent by weight. Preferably, the anti-inflammatory is an extract from *Olax dissitiflora, Aesculus hippocastanum, Centella asiatica, Terminalia sericea, Glycyrrhiza glabra*, or a mixture thereof.

Pharmaceutical or cosmetic compositions may contain the formulation in sufficient amounts to inhibit microbial growth and a pharmaceutically acceptable carrier or excipient. Pharmaceutical, food, or cosmetic compositions can be preserved using the formulation when applied in sufficient amount to inhibit microbial growth. Particularly, a pharmaceutical composition containing the formulation can be used in the treatment of acne.

DETAILED DESCRIPTION OF THE INVENTION

Surprisingly, it has been found that the combination of extracts of some plants naturally having low antimicrobial activity alone or with compounds with antimicrobial activity, leads to a synergistic effect that enhances antimicrobial activity. In particular, combinations including hydrophilic extract of Krameria and lipophilic extract of *Mesua ferrea* have demonstrated superior results against gram positive, gram negative, and anaerobic bacterial strains as compared to compounds lacking extract of Krameria.

The present invention provides several benefits over the conventionally prepared antimicrobial formulations. One embodiment of the present invention enhances the effect of preservatives on food and cosmetic products. Another advantage of the present invention is that the cosmetic and pharmaceutical formulations reduce inflammation. Yet another advantage of the present invention is that the pharmaceutical and cosmetic formulations are particularly effective as antiacne medications.

As used herein, "extract of Krameria" means one or more compounds obtained from the extraction of roots, bark, leaves, or a combination thereof of Krameria with a suitable solvent. The compounds within the formulation obtained by extraction may be hydrophilic, hydrophobic, or a combination thereof. "Extract of Krameria" includes extracts from Krameria sp., *Krameria triandra*, pure compounds from the extract including but not limited to Eupomatenoid 6 and 2-(2,4-dihydroxyphenyl)-5-propenylbenzofuran, and mixtures thereof. Preferably, the extract is from *Krameria triandra* or a pure compound from Krameria extract. Extract of Krameria should be used in an amount which is therapeutically effective to exhibit antimicrobial activity.

As used herein, "pure compound from an extract of Krameria" means neolignanes such as Eupomatenoid 6 and 2-(2,4-dihydroxyphenyl)-5-propenylbenzofuran).

As used herein, "formulation" means a composition including more than one compound which may be homogeneous or heterogenous.

One embodiment of the invention is directed to pharmaceutical and cosmetic formulations with enhanced antimicrobial activity including extracts of Krameria and extracts of *Mesua ferrea* in a sufficient amount to be therapeutically effective. Yet another embodiment of the present invention is directed to formulations including hydrophilic extract of Krameria, lipophilic extracts of *Mesua ferrea,* and substances exhibiting anti-inflammatory activity.

The formulations including extract of Krameria and extract of *Mesua ferrea* exhibiting enhanced antimicrobial activity may be directed to food and cosmetic preservatives and used in the alimentary and cosmetic industries. Formulations, as applied to alimentary or cosmetic industries, include hydrophilic extracts of Krameria, and lipophilic extracts of *Mesua ferrea.*

As used in the present invention, "compounds exhibiting antimicrobial activity" include compounds that are capable of destroying or inhibiting the growth of microorganisms. The compounds exhibiting antimicrobial effect should be used in sufficient amounts to deter microbial growth.

As used in the present invention, "extract of *Mesua ferrea*" include extracts from the flowers, buds, and other parts of the *Mesua ferrea* plant. Extract of *Mesua ferrea* should be used in an amount that is therapeutically effective to exhibit antimicrobial activity; one of ordinary skill in the art with little or no experimentation can determine the amount necessary. When extract of Krameria and extract of *Mesua ferrea* are combined, the formulation ratios of extract of Krameria to extract of *Mesua ferrea* include, but are not limited to, ranges between about 1:10 to about 10:1, preferably in a ratio between about 1:6 to about 6:1, more preferably in a ratio between about 2:3 to about 3:2, and even more preferably in a ratio of about 1:1.

Anti-inflammatory compounds include compounds capable of reducing inflammation. Such anti-inflammatory compounds typically include ximeninic acid, saponins, lauric acid, escin, natural compounds having anti-inflammatory activity, antiacne compounds, and mixtures thereof. Saponins typically include those obtained from *Olax dissitiflora, Aesculus hippocastanum, Centella asiatica, Terminalia sericea, Glycyrrhiza glabra,* or mixtures thereof. Preferably, saponins include *Aesculus hipposatanum* and *Centella asiatica.*

A typical antiacne formulation results in a nearly complete disappearance of acne manifestations and an effective prevention of future acne development. Antiacne formulations comprise of extract of Krameria, extract of *Mesua ferrea,* and natural compounds exhibiting anti-inflammatory activity. Particularly effective is a combination of extract of Krameria, extract of *Mesua ferrea,* ximeninic acid, lauric acid, and at least one saponin. Preferred saponins include those extracted from *Olax dissitiflora, Aesculus hippocastanum, Centella asiatica, Terminalia sericea, Glycyrrhiza glabra,* more preferably those extracted from *Aesculus hippocastanum* and *Centella asiatica*. Additionally, antiacne formulations may have low molecular weight fatty acids such as lauric acid, myristic acid, isomyristic acid or mixtures thereof. The antiacne formulation may also contain additional ingredients commonly used in the art. Additionally, the antiacne formulation can be administered topically including but not limited to gels, lotions, milks, and solid preparations.

Among the various combinations tested for acne treatment and prevention, antiacne formulations with superior clinical results include extract of Krameria, preferably *Krameria triandra,* between about 0.1 percent to about 0.5 percent by weight, extract of *Mesua ferrea* between about 0.1 percent to 0.5 percent by weight, ximeninic acid between about 0.2 percent to about 1 percent by weight, lauric acid between about 0.1 percent to about 0.4 percent by weight, escin between about 0.35 percent to about 1 percent by weight, optionally low molecular weight fatty acids such as lauric acid, myristic acid, isomyristic acid or mixtures thereof.

Preferably a typical antiacne formulation includes extract of Krameria, preferably *Krameria triandra,* between about 0.1 percent to about 0.3 percent by weight, extract of *Mesua ferrea* between about 0.1 percent to about 0.3 percent by weight, ximeninic acid between about 0.4 percent to about 0.7 percent by weight; lauric acid between about 0.1 percent to about 0.3 percent by weight; and escin between about 0.4 percent to about 0.7 percent by weight, and optionally low molecular weight fatty acids such as lauric acid, myristic acid, isomyristic acid or mixtures thereof.

PHARMACOLOGICAL STUDIES

Antiacne activity of the present invention was tested on 30 patients of both sexes, of the age of 18 to 35 years. Patients were treated with 0.5 cm of the formulation twice a day for 45 consecutive days. The untreated part of the face was used as a control. At the end of the treatment, the number of papules, pustoles and comedos (A), the sebum concentration (B), and the presence of *Propioinibacterium acnes* in the exudate from pustoles and comedos (C) were evaluated. The results were tabulated in Table 1.

TABLE 1

| | % REDUCTION | | |
|---|---|---|---|
| TREATMENT | A | B | C |
| None | 5 | 2.3 | 0 |
| Formulation 1 (Ex. IV) | 70 | 13.1 | 80 |
| Formulation 2 (Ex. V) | 50 | 12.4 | 70 |
| Formulation 3* | 20 | 4 | 20 |

*formulation containing ximeninic acid and escin β-sitosterol (EP 283713).

Therefore, the antiacne formulation can be used in pharmaceutical and cosmetic formulations with antiacne activity. The formulations can be applied topically, such as gels, creams, lotions, milk and solid preparation. The formulations can be prepared according to conventional methods well known in the art and as further described by "Remington's Pharmaceutical Handbook," Mack Publishing Co., N.Y., USA. Additionally, the formulations may include additional suitable excipients, in particular antioxidants.

EXAMPLES

Certain embodiments and features of the invention are now illustrated, but not limited, by the following working examples.

Example I

Preparation of the Lipophilic Extract of *Mesua ferrea*

Finely ground buds of *Mesua ferrea* (1 kg) were extracted in a 5 L extractor with $CO_2$ in hyper-critic conditions. A first extraction was carried out at 34° C. and 90 bars of pressure, with about 25 L of carbon dioxide. The resulting extract was discarded and the vegetable material was subjected to a second extraction, at a temperature of 45° C. and pressure of 220 bar. A very thick orange colored oil (15.6 g) was obtained. The oil can be used directly as such or subjected to further fractionations by means of conventional chemical separations.

Example II

Preparation of the Lipophilic Extract of *Krameria triandra*

The bark of the root of *Krameria triandra* (2 kg), after grinding, was extracted three times with 5 L of acetone. The combined extracts were concentrated, reduced in volume, and the concentrate was taken up in 0.8 L of acetone:water 1:1 (v/v). The resulting suspension was extracted twice with 0.5 L of methylene chloride. The organic phase was dried over anhydrous sodium sulfate, and concentrated to dryness. A reddish solid (85 g) was obtained, containing about 26 percent of Eupomatenoid 6 and 14 percent of 2-(2,4-dihydroxyphenyl)-5-propenylbenzofuran.

Example III

Preparation of the Extract of *Mesua ferrea* with Hexane

Finely ground buds of *Mesua ferrea* (1 kg) was extracted 4 times with 2 L of hexane under reflux. The combined hexane extracts were decolorized with active charcoal (5 g) and concentrated under vacuum to form an oil. Extract (14.5 g) was obtained. The extract may used without further fractionation.

EXAMPLE IV

| Preparation of a Water/Silicon emulsion | |
|---|---|
| Mesua Ferrea | 0.25 g |
| Krameria triandra | 0.2 g |
| Ximeninic Acid | 0.6 g |
| Lauric Acid | 0.2 g |
| 18-β Glycyrrhetic acid | 0.5 g |
| Propylene glycol | 5 g |
| Sodium Coccoylglutamte 25 percent sol. | 2 g |
| Mineral oil and lanolin alcohols | 2.5 g |
| Octyl Octanoate | 5 g |
| Octododecyl Myristate | 7.5 g |
| Cetyl Dimethycone Copolyol | 2.5 g |
| Tetramer Cyclomethicone | 5 g |
| Sodium Chloride | 2 g |
| Glycerin | 2 g |
| Imidurea | 0.3 g |
| Methylparaben | 0.1 g |
| Purified Water q.s. to | 100 g |

EXAMPLE V

| Preparation of an oil/water emulsion | |
|---|---|
| Krameria Triandra | 0.2 g |
| Escin β-Sitosterol fitosome ® | 0.5 g |
| Ximeninic acid | 0.5 g |
| Lauric Acid | 0.2 g |
| Gliceryl Monostearate | 3 g |
| Alkyl $C_{12}$-Benzoate | 7 g |
| Silicon Oil | 0.5 g |
| Carbomer | 0.5 g |
| Acrylate/$C_{10-30}$ Alkylacrylate Crosspolymer | 0.2 g |

EXAMPLE V-continued

| Preparation of an oil/water emulsion | |
|---|---|
| Sodium Lauryl Sulfate | 1 g |
| Propylene glycol | 5 g |
| Sodium hydroxide 10 percent sol. | 1.5 g |
| Imidurea | 0.3 g |
| Methylparaben | 0.1 g |
| Purified water q.s. to | 100 g |

EXAMPLE VI

| Preparation of an oil/water emulsion | |
|---|---|
| Krameria Triandra | 0.25 g |
| Escin β-Sitosterol fitosome ® | 0.5 g |
| Lauric Acid | 0.2 g |
| Polyglyceryl 8-pentastearate and behenyl alcohol and sodium stearoyl lactylate (Nikkomulese 41 - Nikkho) | 2.5 g |
| Behenyl Alcohol | 1.5 g |
| Squalene | 7 g |
| Trioctanoine | 6 g |
| PPG-12/SMDI | 2 g |
| Butenyl glycol | 5 g |
| Xanthan gum | 0.3 g |
| Preservatives | q.s. |
| Purified water q.s. to | 100 g |

Table 2 shows the average values of the in vitro antimicrobial activity of two exemplary extracts. The first is prepared from *Krameria triandra* and from *Mesua ferrea*. The activity, expressed in M.I.C. (minimum inhibitory concentration), was evaluated by normal terms within the art. Moreover, one of ordinary skill in the art with little or no experimentation can optimize the results for a particular antimicrobial compound or mixtures of compounds.

TABLE 2

In Vitro Antimicrobial Activity of the Standardized Extracts of Krameria Triandra and Mesua Ferrea.

| | M.I.C. μg/ml | | | |
|---|---|---|---|---|
| Microbial strains | I | II | III | IV |
| *Staphilococcus aureus* MPR5 | 6.1 | 4 | 2 | 1 |
| *Staphilococcus aureus* ATCC6538 | 12 | 7 | 3 | 0.5 |
| *Staphilococcus aureus* F2 ISF 3 | 9 | 15 | 4 | — |
| *Staphilococcus epidermis* HCF Berset C | 10 | 8 | 4 | — |
| *Staphilococcus epidermis* CPHL | 8 | 6 | 3 | 1 |
| *Streptococcus feaecalis* LEP Br | 10 | 6 | 2 | 16 |
| *Escherichia coli* CNUR 1 | >128 | >128 | 32 | 0.51 |
| *Acinetobacter cal.* OSMPV | 6.2 | 4 | 2 | 2 |
| *Pseudomonas aeruginosa* CNUR 4 | 6 | 4.3 | 1 | 32 |
| *Trichophyton mentagrophytes* 193 | 128 | 61 | 12 | 2 |
| *Candida albicans* ATCC 10231 | 62.5 | 128 | 12 | 2 |
| *Bacteroides fragilis* | 26 | 16 | 4 | 32 |
| *Propionibacterium acnes* | 4 | 4 | 1 | 32 |

I = extract of *Krameria triandra* prepared according to example II
II = extract of *Mesua ferrea* prepared according to example I
III = 1:1 combination of *Krameria triandra* and *Mesua ferrea*
IV = rufloxacin for bacterial, miconazole for fungi.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An antiacne composition comprising:

a hydrophilic extract of Krameria;

at least one acid selected from the group consisting of ximeninic acid and lauric acid; and at least one anti-inflammatory compound, wherein the extract is present in an amount sufficient to inhibit acne manifestations.

2. The composition of claim 1, wherein the extract of Krameria is obtained by extracting one or more of the roots, bark, or leaves of Krameria with a protic solvent or acetone.

3. The composition of claim 1, wherein the extract of Krameria is present in an amount from about 0.1 percent to about 0.5 percent by weight.

4. The composition of claim 2, wherein the extract of Krameria is an extract of *Krameria triandra*.

5. The composition of claim 4, wherein the extract of *Krameria triandra* is present in an amount from about 0.1 percent to about 0.3 percent by weight.

6. The composition of claim 1, wherein the extract of Krameria is a pure compound of the extract.

7. The composition of claim 6, wherein the pure compound of the extract contains one or more neolignanes comprising Eupomatenoid 6,2-(2,4-dihydroxyphenyl)-5-propenylbenzofuran, or a mixture thereof.

8. The composition of claim 1, wherein the at least one acid is ximeninic acid and is present in an amount from about 0.2 percent to about 1 percent by weight.

9. The composition of claim 1, wherein the at least one acid is lauric acid and is present in an amount from about 0.1 percent to about 0.4 percent by weight.

10. The composition of claim 1, wherein ximeninic acid is present in an amount from about 0.2 percent to about 1 percent by weight and lauric acid is present in an amount from about 0.1 percent to about 0.4 percent by weight.

11. The composition of claim 1, wherein the at least one anti-inflammatory compound is a saponin present in an amount from about 0.1 percent to about 1 percent by weight.

12. The composition according to claim 11, wherein the at least one anti-inflammatory saponin is an extract from *Olax dissitiflora, Aesculus hippocastanum, Centella asiatica, Terminalia sericea, Glycyrrhiza glabra,* or a mixture thereof.

13. The composition of claim 12, wherein the at least one anti-inflammatory saponin is escin.

14. The composition of claim 13, wherein the escin is present in an amount from about 0.4 percent to about 0.7 percent by weight.

15. The composition of claim 1, further comprising at least one low molecular weight fatty acid.

16. The composition of claim 15, wherein the at least one low molecular weight fatty acid comprises myristic acid, isomyristic acid, or a mixture thereof.

17. The composition of claim 1, wherein the composition is a gel, lotion, milk, or solid.

18. A method of treating acne on a body which comprises applying thereto a composition comprising:

a hydrophilic extract of Krameria;

at least one of ximeninic acid or lauric acid; and at least one anti-inflammatory saponin, wherein the composition is applied in an amount sufficient to treat, inhibit, or prevent acne manifestations on the body.

* * * * *